(12) United States Patent
Dennehey et al.

(10) Patent No.: US 6,497,685 B1
(45) Date of Patent: Dec. 24, 2002

(54) INTEGRAL INTRAVENOUS CHAMBER AND FILTER

(75) Inventors: T. Michael Dennehey, Arlington Heights, IL (US); Birendra K. Lal, Lake Zurich, IL (US); Massimo Scagliarini, Bologna (IT)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/534,674

(22) Filed: Mar. 24, 2000

(51) Int. Cl.[7] .................. A61M 5/165; B01D 29/11
(52) U.S. Cl. ............... 604/252; 210/448; 210/450; 210/451
(58) Field of Search ................. 604/252, 251; 210/435, 437, 451, 450, 448

(56) References Cited

U.S. PATENT DOCUMENTS

| | | |
|---|---|---|
| 3,004,536 A | 10/1961 | Walter |
| 3,217,889 A | 11/1965 | Berg |
| 3,593,854 A | 7/1971 | Swank |
| 3,664,339 A | 5/1972 | Santomieri |
| 3,722,697 A | 3/1973 | Burke et al. |
| 3,765,536 A | 10/1973 | Rosenberg |

(List continued on next page.)

FOREIGN PATENT DOCUMENTS

| | | |
|---|---|---|
| DE | 2926434 C2 | 3/1984 |
| DE | 3509420 A1 | 9/1986 |
| DE | 3722562 A1 | 1/1989 |
| DE | 3643092 C2 | 5/1989 |
| DE | 4108015 A1 | 9/1992 |
| DE | 4122241 A1 | 1/1993 |
| EP | 0 007 601 B1 | 7/1979 |
| EP | 0 033 080 A2 | 1/1981 |
| EP | 0 235 315 A1 | 9/1987 |
| EP | 0 305 687 B1 | 3/1989 |
| EP | 0 516 846 A1 | 12/1992 |
| EP | 0 765 727 A2 | 4/1997 |
| FR | 1077115 | 11/1954 |
| GB | 822 195 | 10/1959 |
| GB | 1 221 625 | 2/1971 |
| GB | 1 230 487 | 5/1971 |
| GB | 1 260 949 | 1/1972 |
| GB | 1 517 731 | 7/1978 |
| GB | 2 000 685 A | 1/1979 |
| GB | 1 543 591 | 4/1979 |
| GB | 2 006 035 A | 5/1979 |
| GB | 1 575 751 | 9/1980 |
| GB | 1 590009 | 5/1981 |
| GB | 2 083 757 A | 3/1982 |
| GB | 2 101 908 A | 1/1983 |
| GB | 2 183 168 B | 10/1989 |
| GB | 2 186 799 B | 3/1990 |
| GB | 2 238 374 A | 5/1991 |
| WO | 83/03364 | 10/1983 |
| WO | WO 92/10483 | 2/1992 |

OTHER PUBLICATIONS

International Search Report, Application No. PCT/US/01/09558 dated Sep. 29, 2001.

*Primary Examiner*—Kevin Lee
(74) *Attorney, Agent, or Firm*—Jeffrey C. Nichols; Mark J. Buonaiuto; Francis C. Kowalik

(57) ABSTRACT

A filtering chamber for a set for the administration of fluids is provided. The chamber includes a housing providing a passageway for the fluid in the administration set. Within the chamber is a filter of screen which filters the fluid flowing through the housing. The filter or screen is attached to the housing during molding of the housing without the use of bonding agents, resulting in a chamber component which may be produced automatically and economically.

12 Claims, 8 Drawing Sheets

U.S. PATENT DOCUMENTS

| | | |
|---|---|---|
| 3,765,537 A | 10/1973 | Rosenberg |
| 4,014,329 A | 3/1977 | Welch et al. |
| 4,056,476 A | 11/1977 | Mouwen et al. |
| 4,087,363 A | 5/1978 | Rosemeyer et al. |
| 4,161,504 A | 7/1979 | Baldini |
| 4,162,220 A | 7/1979 | Servas |
| 4,306,973 A | 12/1981 | Ishikawa et al. |
| 4,336,036 A | 6/1982 | Leeke et al. |
| 4,450,078 A | 5/1984 | Walker et al. |
| 4,547,190 A | 10/1985 | Leason |
| 4,565,665 A | 1/1986 | Fogt |
| 4,631,050 A | 12/1986 | Reed et al. |
| 4,695,382 A | 9/1987 | Cronin |
| 4,734,269 A | 3/1988 | Clarke et al. |
| 4,810,378 A | 3/1989 | Carmen |
| 4,850,964 A | 7/1989 | Cotter |
| 4,954,251 A | 9/1990 | Barnes et al. |
| 5,064,542 A | 11/1991 | Negersmith et al. |
| 5,137,624 A | 8/1992 | Klotz |
| 5,252,204 A | 10/1993 | Chiodo |
| 5,266,194 A | 11/1993 | Chiodo |
| 5,344,561 A | 9/1994 | Pall et al. |
| 5,417,906 A | 5/1995 | Chiodo |
| 5,489,385 A | 2/1996 | Raabe et al. |
| 5,902,281 A * | 5/1999 | Kraus et al. ............... 604/252 |

* cited by examiner

INTEGRAL INTRAVENOUS CHAMBER AND FILTER

BACKGROUND OF THE INVENTION

Frequently surgical operations and other medical procedures and treatments require the intravenous infusion of fluids such as whole blood or whole blood products. The infusion is typically accomplished by an administration set which provides a fluid path between a container of the fluid and a catheter which extends through a patient's skin and into a vein or artery.

These fluids must be acceptable for infusion upon administration. Although the fluids are generally packaged in a formulation which is appropriate for infusion, filtering of the fluid after the fluid leaves the container but before administration is frequently desired. In particular, whole blood may produce fibrin accumulations and clumped cells during storage which should be removed prior to administration of the whole blood. Thus administration sets for intravenous fluids including blood will typically include a filter element along the flow path established by the administration set.

Generally administration sets include a filter element within a component referred to as a drip chamber. The drip chamber is generally tubular and has an upper end cap and lower end cap attached to opposite ends of a chamber. The upper end cap will contain a means for establishing a fluid connection with the upstream portion of the administration set and the lower end cap will contain a means for establishing a fluid connection with the downstream portion of the administration set. Typically flexible tubing will be connected to the upper and lower end caps; however, other components of the administration set may be directly attached to the end caps. For example, a spike for accessing an administration port of a flexible container of fluid may be attached to the upper end cap.

At the upper end cap is typically a drop former which is designed to produce droplets of a desired volume of the fluid as the fluid flows through the upper end cap and into the chamber. Then by adjusting the flow of fluid so that a desired number of droplets enter the chamber over a certain period of time, a desired rate of volume administration may be accomplished.

A filter element is generally placed within the chamber for filtering the fluid before the fluid exits the chamber. The filter element and chamber walls are generally configured so that all fluid which flows through the chamber must flow through the filter element before the fluid exits the chamber.

In most prior art chambers, the filter is a separate element which must be attached to the other parts of the chamber during assembly. The two most common method of attachment are bonding with either a solvent or adhesive or a press fit. Each option has drawbacks. For example, bonding introduces a bonding agent into the materials which must be acceptable from a clinical standpoint and the bonding step adds cost to the construction of the filtering chamber.

Use of press fit components may make the chamber rigid, and hinder the ability of a health care provider to flex the chamber walls during priming. Also this flexing may contribute to the dislodging of the press fit parts. In addition press fit may require the addition of other parts to insure that the parts are properly attached to each other.

Thus it is an object of the present invention to provide a drip chamber which filters fluid flowing through the chamber and may be economically constructed in a manner which facilitates use by a health care provider. More particularly includes a filtering element which may be attached to the chamber without use of a bonding agent or through a press fit configuration or additional parts.

SUMMARY OF THE INVENTION

The present invention generally accomplishes the objectives by providing a filter chamber in which a filter element is attached to a chamber during the molding process of the chamber. More particularly the present invention provides a filter chamber having a chamber which forms a passageway for the flow of fluid through the filter chamber. The filter chamber also includes a filter element and the filter element and chamber are configured and arranged so that a portion and preferably all the fluid flowing through the filter chamber flow through the filter element. The filter element is attached to the chamber during the molding of the chamber. More particularly the filter element is attached to the chamber when the material forming the chamber hardens about one of more portions of the filter element during the molding process of the chamber so that the filter is arranged and supported in the desired position and configuration.

DESCRIPTION OF THE PREFERRED EMBODIMENT

Figure 1:
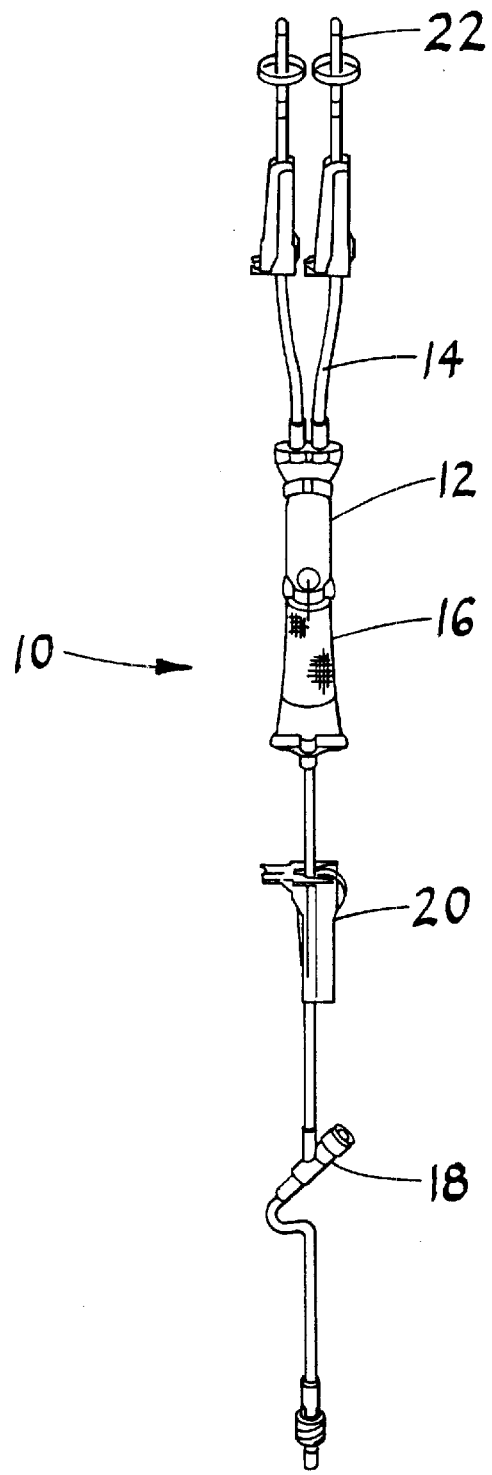
FIG. 1 is a front planar view of a prior art administration set having a chamber with a filter element.

Referring to FIG. 1 a prior art administration set 10 including a filter chamber 12 is generally shown. The set 10 includes flexible tubular components 14 and other components which may vary depending on the application. Such other components may include a drip chamber with filter element 16, y-site 18, roller clamp and spike connector 22. Set 10 is generally sterilized so that the passageway for fluid flowing through the set is sterile to prevent any contamination of the fluid as it flows through the set. The set 10 is then generally packaged in a manner to maintain the sterility prior to use.

Figure 2:
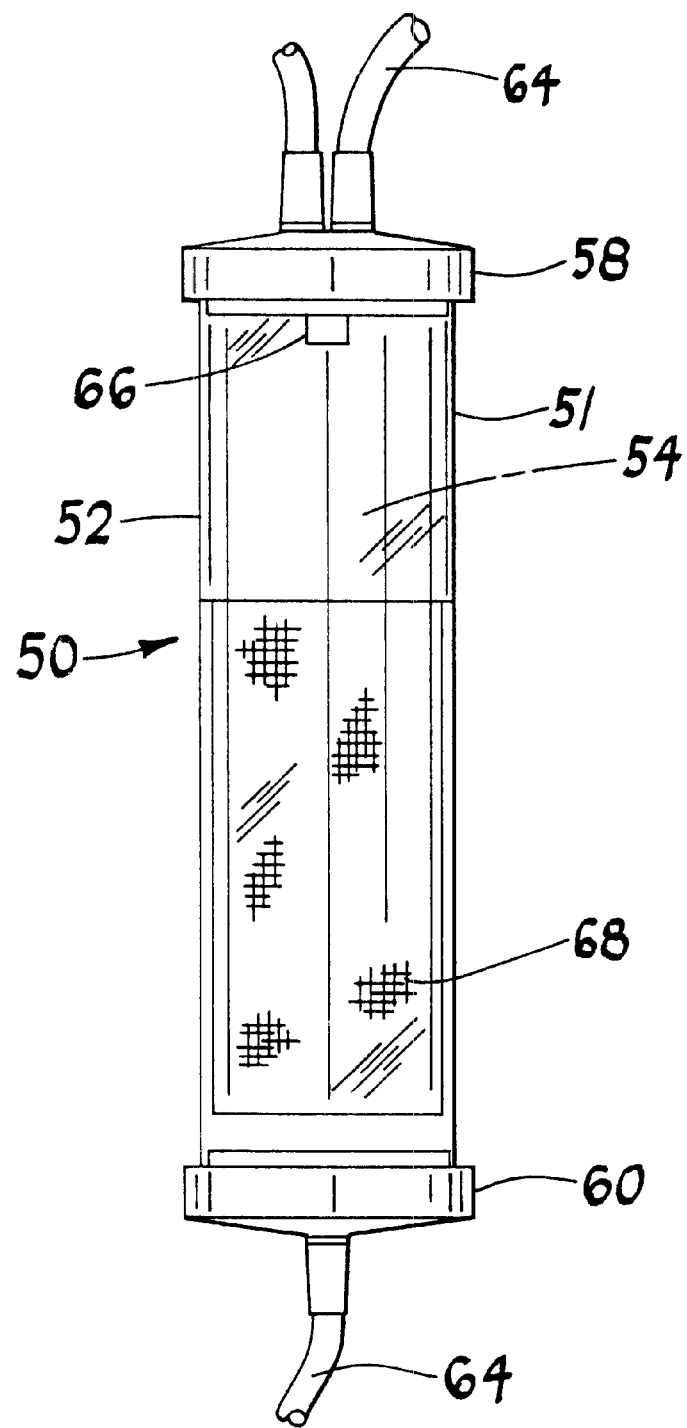
FIG. 2 is a front planar view of a preferred embodiment of a drip chamber of the present invention which may be substituted for the chamber with filter element of FIG. 1.

Referring to FIG. 2, a preferred embodiment of a drip chamber of the present invention suitable for high volume administration of fluids is generally shown at 50. The drip chamber 50 is suitable for replacing the drip chamber 12 with filter element 16 (FIG. 1). The drip chamber 50 includes a housing 51 having sidewalls 52 which forms a passageway 54 for the flow of fluid through an administration. The sidewalls 52 are preferably formed so as to be transparent thereby allowing the user to see into the passageway 54.

The drip chamber 50 includes an upper end cap 58 and a lower end cap 60, to seal the ends of the housing 51 and form a means for connection to the upstream and downstream components of the set 10 (FIG. 1). In the shown preferred embodiment shown the upper end cap 58 and lower end cap 60 are shown as attached to flexible tubing 64. However, it should be understood that either the upper end cap 58 or lower end cap 60 may be directly attached to other components. Also, in one embodiment a spike connector 22 (FIG. 1), which may be used to access the administration port of a solution container (not shown) is integrated with the upper end cap 58, to eliminate one component.

Also, either the upper end cap 58 or lower end cap 60 may be configured so that a plurality of components may be attached thereto. For example, the upper end cap 58 may be modified to establish a fluid connection with two separate flexible tubing 64, where one of the tubing forms a passageway for a flushing solution.

The upper end cap 58 also includes a drop former 66 to form drops of a generally constant volume so that the flow of fluid through the passageway 54 may be monitored and adjusted.

Within the passageway 54 of the drip chamber 50, a filter or screen element 68 to filter the fluid flowing through the drip chamber is positioned. The screen element 68 is attached to the sidewalls 52 during the molding of the sidewalls so that use of an attachment step such as attaching with bonding agents or press fit of additional components is eliminated. This attachment of the screen element 68 during the molding of the sidewalls 52 leads to less expensive production of the drip chamber 50.

Figure 3:
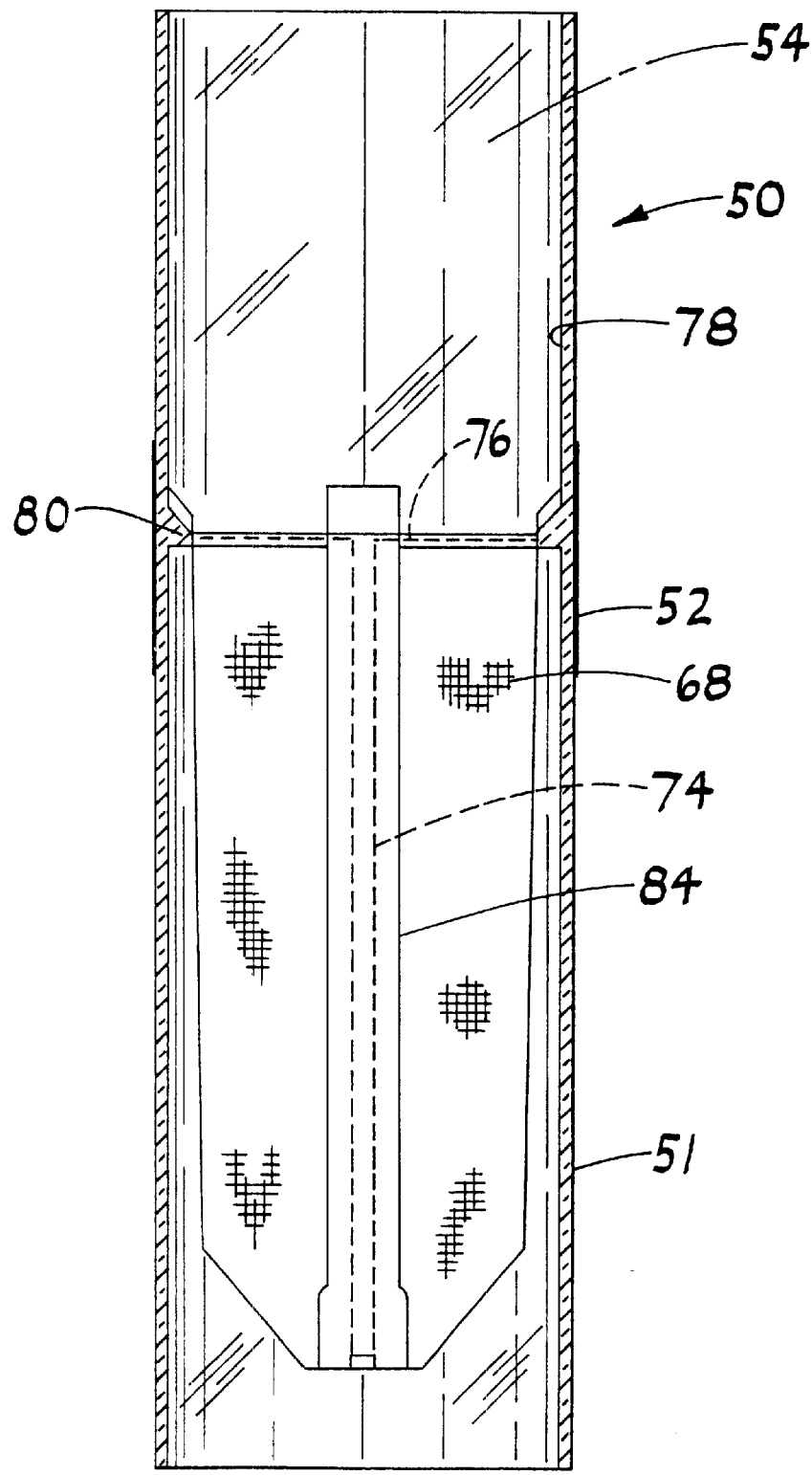
FIG. 3 is a partial sectional view of the drip chamber set of FIG. 2.
Figure 4:
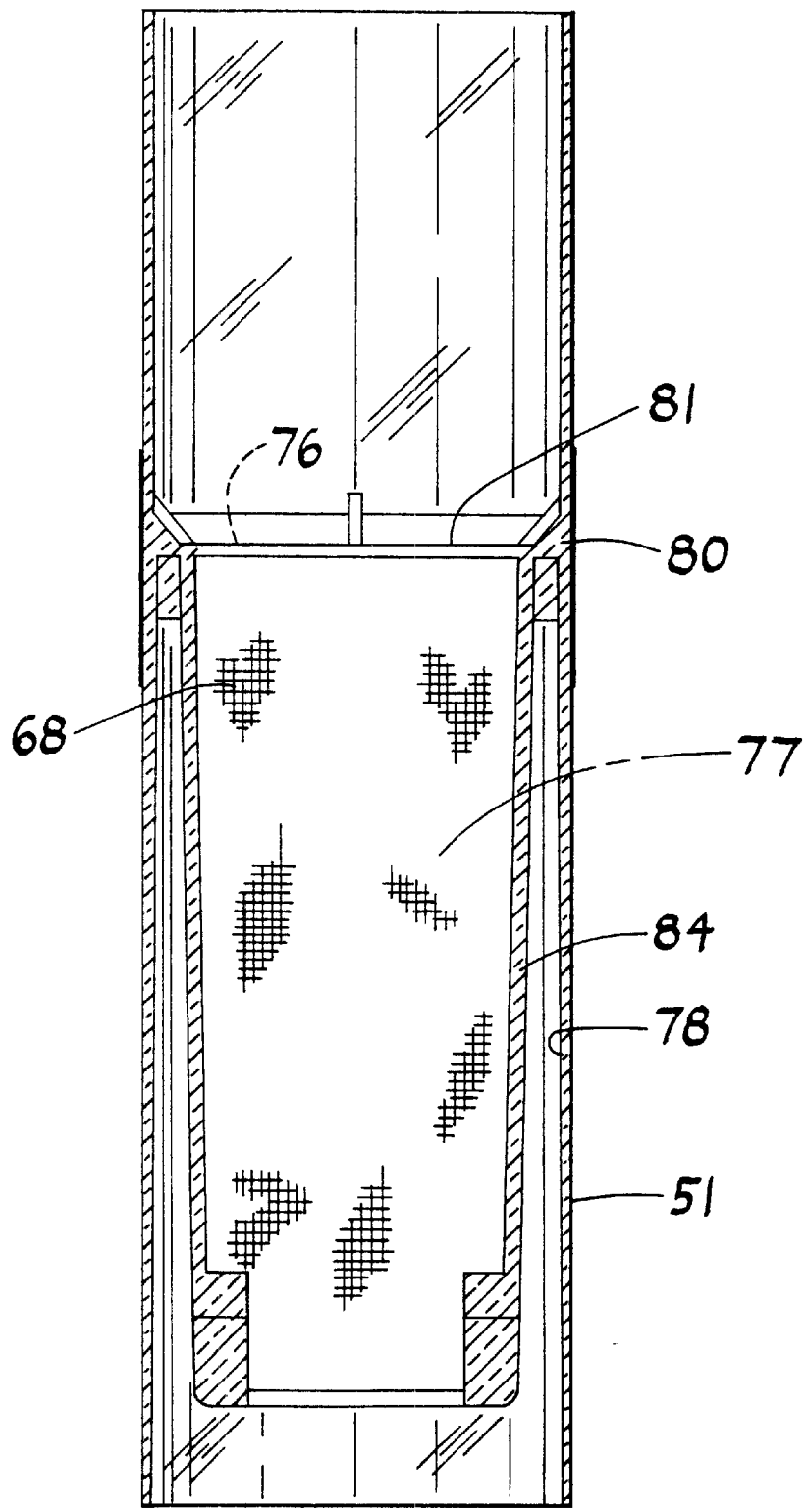
FIG. 4 is an additional partial sectional view of the drip chamber of FIG. 2, rotated 90° from the view shown in FIG. 3.

Referring to FIG. 3 and FIG. 4, the screen element 68 is configured and attached to the sidewalls 52 so that all of the fluid flowing through the drip chamber 50 flows through the screen element for filtering. It may be understood that the screen element 68 may be attached in such a manner so that only a portion of the fluid flowing through the drip chamber 50 flows through the screen. In the preferred embodiment, the screen element 68 is generally of a shape that can be formed into an extended tubular sack having side edges 74 and a top edge 76 and an interior 77. The top edge 76 is attached to the sidewalls 52 circumferentially around the inside surface 78 of the sidewalls during molding of the sidewalls. A thickened section 80 extending radially about the sidewalls 52 is formed during molding of the sidewalls 52 and the top edge 76 of the screen element 68 is sealingly encased in the thickened section.

In the preferred embodiment, the thickened section 80 may be formed with a tapered cross section to direct the flow of fluid through an opening 81 defined by the top edge 76 and into the interior 77 of the screen element 68.

Figure 5:
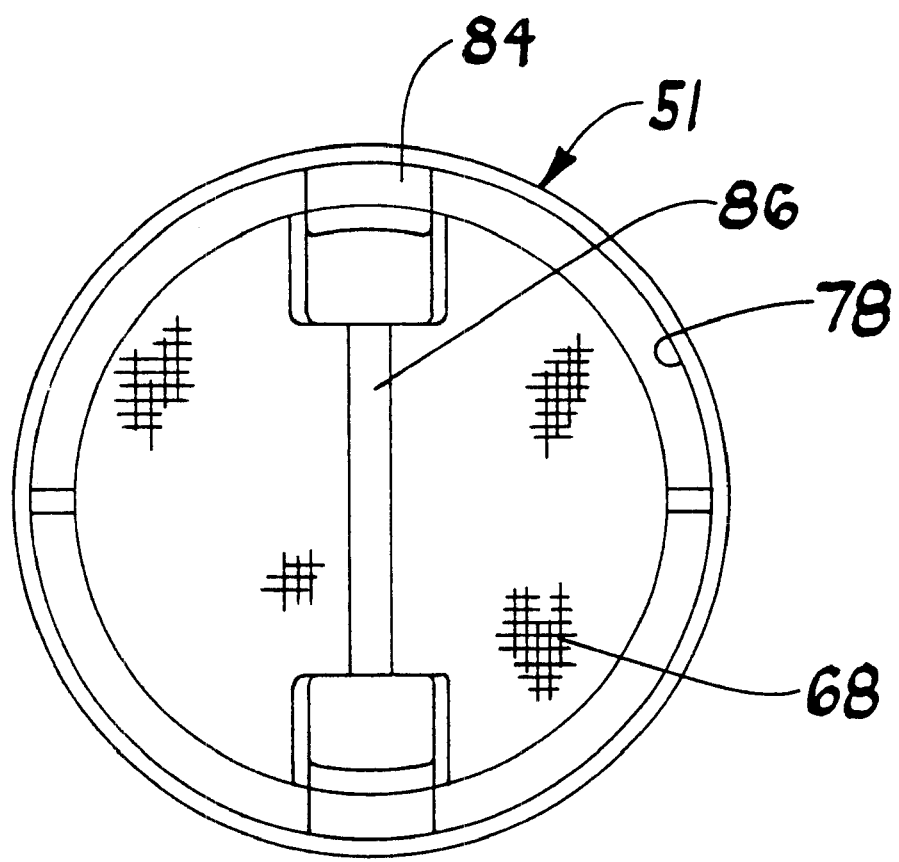
FIG. 5 is a lower planar view of the drip chamber shown in FIG. 3.

Downwardly depending arm portions 84 of the thickened section 80 of the housing 51 are integrally formed during molding of the housing 51 and the arm portions encase the side edges 74 of the element 68. The arms 84 are integrally attached to the thickened section 80 and extend along the inner surface 78 of the side walls toward the lower end cap 60 (FIG. 2). Referring also to FIG. 5, to provide support to the screen element 68, a support member 86 is formed during molding which attaches the lower ends of the arms 84 to each other. It should be understood that other configurations of filter or screen elements and attachment arrangements are also possible such that the screen element 68 is configured and positioned while being integrally attached to the housing 51 so that all or a portion of the fluid flows through the screen element 68 as it flows through the passageway 54 defined by the housing.

Figure 6:
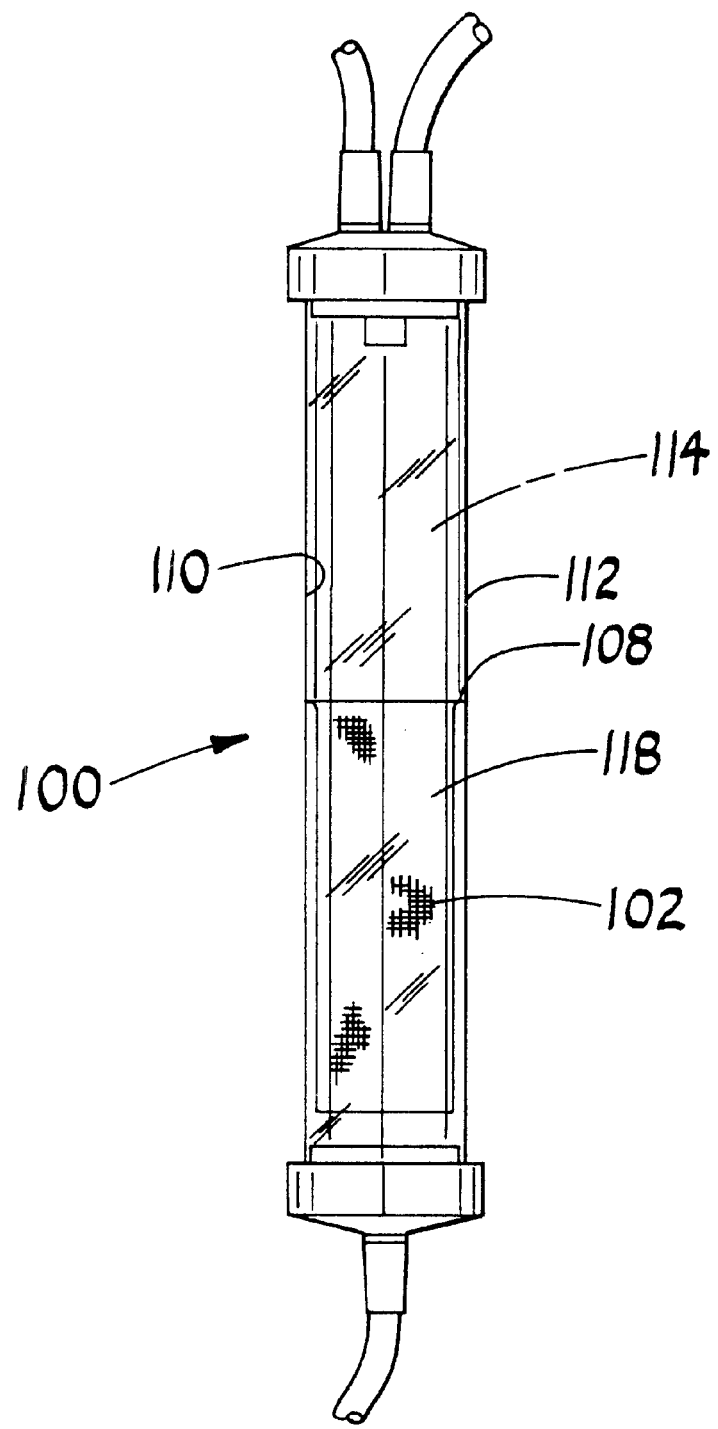
FIG. 6 is an alternate preferred embodiment of the drip chamber of FIG. 2.

Referring to FIG. 6 an alternate preferred embodiment of a drip chamber of the present invention is generally indicated at 100. The chamber 100 is smaller in size and particularly suited to the filtering of smaller volumes of fluid. The drip chamber 100 is similar to the drip chamber 50 (FIG. 2) except a screen element 102 is configured in a manner which increases the surface area of the screen to reduce the potential for clogging.

Figure 7:
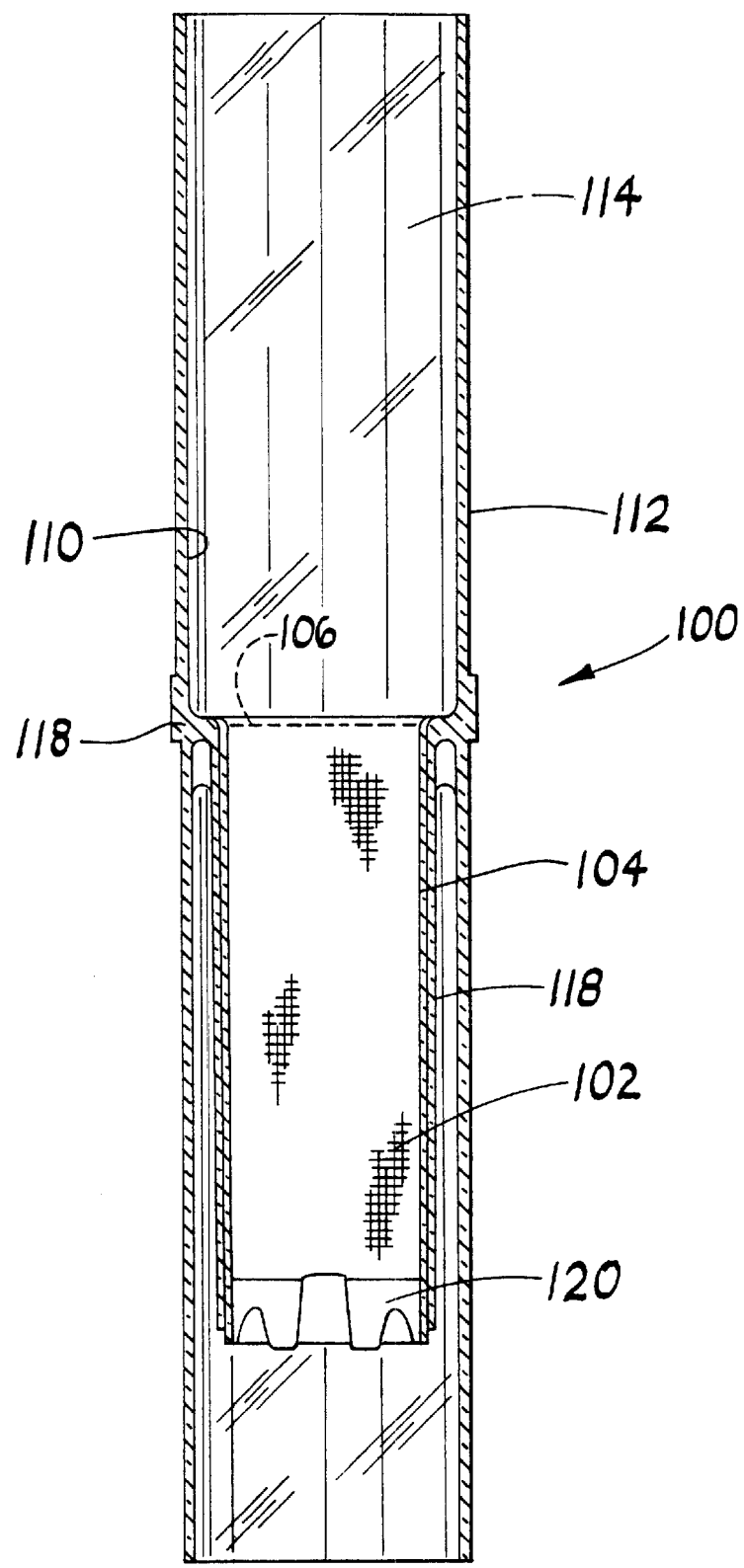
FIG. 7 is a partial sectional view of a portion of the drip chamber of FIG. 6.
Figure 8:
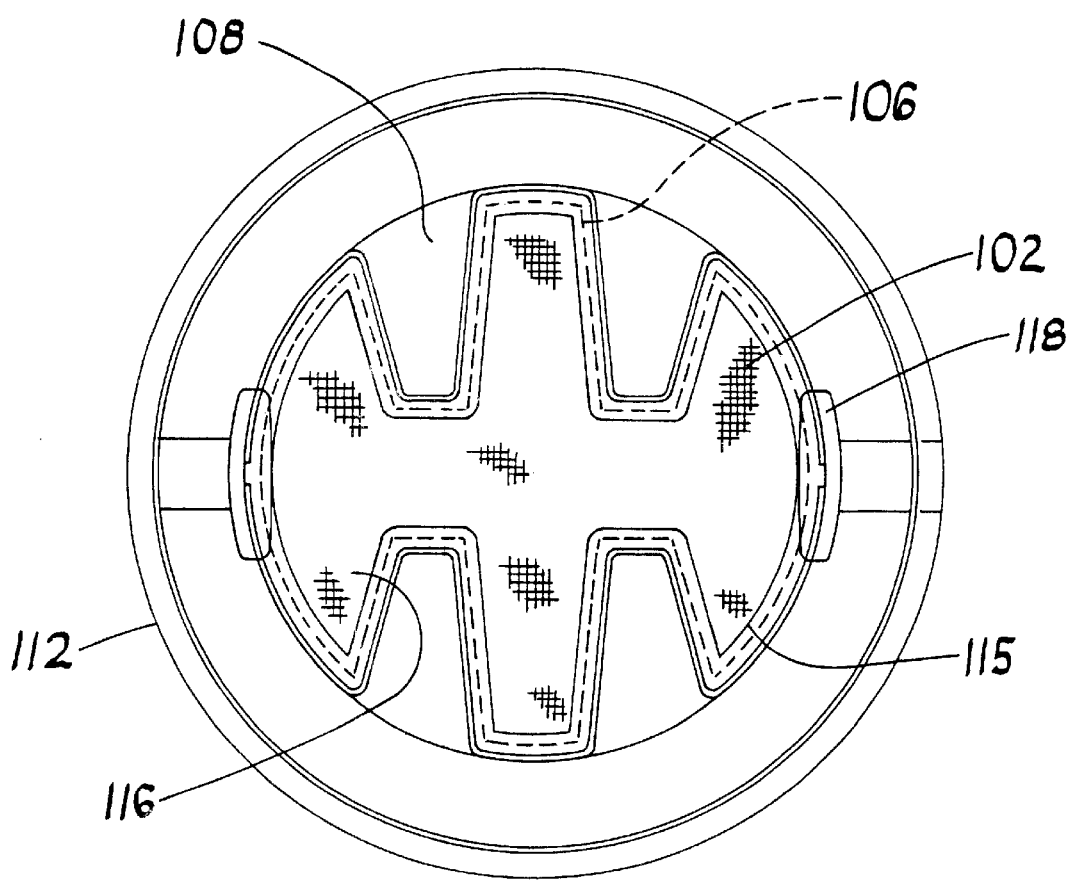
FIG. 8 is a top planar view of the drip chamber of FIG. 7.

Referring to FIG. 7 and FIG. 8, more particularly, the screen element 102 is forming in a generally corrugated sack like configuration having side edges 104 and a top edge 106. More particularly, the screen element 102 is formed with a star shaped periphery when viewed in a direction generally along the passageway. The top edge 106 is sealingly encased in a radial flange 108 forming a part of the housing 112. Side walls 110 of the housing 112 form a passageway 114 for the flow of fluid through the drip chamber 100. The radial flange 108 forms an opening 115 into an interior 116 defined by the screen element 102. The opening 116 is shaped similar to the shape of the top edge 106 in the transverse direction, and preferably in the star shaped configuration of the screen element 102.

Arm portions 118 of the housing 112 are formed along with the flange 108 during molding and the arms 118 extend downward from the flange. The arms 118 sealingly encase the opposing side edges 104 of the screen element 102. A support member 120 is attached to and extends between the lower ends of the side arms 118 along the bottom end of the screen element 102. The support member 120 is also formed during the molding of the housing 112.

Thus, the screen element 102 is configured and attached to the housing 112 during molding of the housing 112. Also, the screen element 102 and side walls 110 are attached to each other so that at least a portion and preferably all the fluid flowing through the passageway 114 formed by the housing 112 flows through the screen element.

Referring to both FIGS. 3 and 7, in manufacturing the preferred embodiment the housing 51, 112 with screen element 68, 102 is injection molded utilizing an insert molding process to integrally incorporate the woven screen element into the housing. The screen material is delivered and formed into the shape of the finished screen element 68, 102. The screen element 68, 102 is then entrapped and supported within the injection mold (not shown). When the mold closes, the melted plastic material is injected into the mold cavity to form the housing 112, 51 and encasing the edges of the screen material in the configuration of the shaped screen element 68, 102. The edges of the screen element 68, 102 are enclosed with the polymeric material of the housing 51, 112. The polymeric material seals about the edges so as to force a portion and preferably all fluid flowing through the passageway to flow through the screen element 68, 102.

The mold is cooled to reduce the temperature of the molten plastic, solidifying it in the configuration of the predefined housing design. The mold may be cooled utilizing one of several techniques such as water, air or a combination of water and air cooling. In the preferred embodiment the housing 51, 112 is formed with a long thin walled tubular shape which facilitates manipulation of the housing to aid in priming of the set. However, the long, thin walled tubular shape of the housing 51, 112 hinders ejection from the mold.

To facilitate the ejection of the housing 51, 112 and screen element 68 102 from the mold, the mold utilizes a special non-stick surface treatment to minimize sticking. The molded housing 51 112 and attached screen element 68, is ejected from the mold utilizing a sleeve, pin, air or a combination thereof.

In the preferred embodiment, the housing 51, 112 is formed of a SB Block Copolymer and preferably a combination of modified styrenes produced by BASF, Shell Oil or Phillips petroleum. The screen element 68, 102 is preferably a polyester material.

In use, referring to FIG. 1 in conjunction with FIG. 2, the health care practitioner establishes a fluid connection with a solution container (not shown) utilizing the spike 22. The practitioner then begins to squeeze the sidewalls 52 of the housing 51 to prime the set. Fluid flows through the flexible tubing 64, upper end cap 58 and drop former 66 and into the passageway 54. The fluid is then forced by the sidewalls 52, thickened section 80 and arm portions 84 to flow through the filter or screen element 68, to filter out any undesired particles. The fluid then flows out of the housing 51 through the lower end cap 60. After priming, the fluid flows though the drip chamber 50 in a similar manner as the priming fluid.

It will be understood that the embodiments of the present invention which have been described are illustrative of some of the applications of the principles of the present invention. Those skilled in the art may make various modifications without departing from the true spirit and scope of the invention.

What is claimed is:

1. A filter chamber component for filtering fluid flowing through an administration set, said filter chamber component comprising:

a generally tubular housing having an inlet for receiving fluid into the housing, an outlet for exhausting fluid from the housing, and a side wall defining a passageway through which fluid flows from the inlet toward the outlet of the housing, said side wall having a thickened portion extending laterally inward therefrom into the passageway; and a filter element having a sack configuration including an open end, a closed end and a side wall therebetween, said filter element being disposed within the passageway and being molded into the thickened portion of the side wall generally at the open end of the filter element such that at least a portion of the fluid flowing through the passageway flows through the filter element to filter the fluid.

2. A filter chamber component as set forth in claim 1 wherein the passageway has a cross-sectional area upstream of the thickened portion of the housing side wall which is substantially equal to a cross-sectional area of the passageway downstream of the thickened portion of the housing side wall.

3. A filter chamber component as set forth in claim 2 wherein the thickened portion of the housing side wall is tapered for directing fluid flowing through the passageway to flow through the open end of the filter element.

4. A filter chamber component for filtering fluid flowing through an administration set, said filter chamber component comprising:

a generally tubular housing having an inlet for receiving fluid into the housing, an outlet for exhausting fluid from the housing, and a side wall defining a passageway through which fluid flows from the inlet toward the outlet of the housing; and a filter element having a sack configuration including an open end, a closed end and a side wall therebetween, said filter element being disposed within the passageway and being molded into the housing side wall intermediate the inlet and the outlet of the housing generally at the open end of the filter element such that at least a portion of the fluid flowing through the passageway flows through the filter element to filter the fluid, the passageway having a cross-sectional area upstream of the open end of the filter element which is substantially equal to a cross-sectional area of the passageway downstream of the open end of the filter element.

5. A filter chamber component for filtering fluid flowing through an administration set, said filter chamber component comprising:

a generally tubular housing having an inlet for receiving fluid into the housing, an outlet for exhausting fluid from the housing, and a side wall defining a passageway through which fluid flows from the inlet toward the outlet of the housing, said side wall having a flange formed integrally therewith and extending radially inward therefrom; and a filter element having a sack configuration including an open end, a closed end and a side wall therebetween, said filter element being disposed within the passageway and being molded into the flange of the housing generally at the open end of the filter element such that substantially all of the fluid flowing through the passageway from the inlet of the housing toward the outlet passes through the filter element to filter the fluid.

6. A filter chamber component as set forth in claim 5 wherein the passageway has a cross-sectional area upstream of the flange which is substantially equal to a cross-section of the passageway downstream of the flange.

7. A filter chamber component for filtering fluid flowing through an administration set, said filter chamber component comprising:

a generally tubular housing having an inlet for receiving fluid into the housing, an outlet for exhausting fluid from the housing, and a side wall defining a passageway through which fluid flows from the inlet toward the outlet of the housing; and a filter element having a sack configuration including an open end, a closed end and a side wall therebetween, said filter element being disposed within the passageway and being molded into the housing side wall generally at the open end of the filter element such that at least a portion of the fluid flowing through the passageway flows through the filter element to filter the fluid, the side wall of the filter element having corrugations formed therein wherein at least one of the corrugations is sufficiently exposed to fluid flowing within the passageway to permit fluid to flow through the filter element generally at said at least one corrugation.

8. A filter chamber component as set forth in claim 7 wherein at least one of said corrugations projects radially inward of the filter element side wall.

9. A filter chamber component as set forth in claim 7 wherein the filter element has a generally star-shaped cross-section.

10. A filter chamber component for filtering fluid flowing through an administration set, said filter chamber component comprising:

a generally tubular housing having an inlet for receiving fluid into the housing, an outlet for exhausting fluid from the housing, and a side wall defining a passageway through which fluid flows from the inlet toward the outlet of the housing;

a filter element having a sack configuration including an open end, a closed end and a side wall therebetween, said filter element being disposed within the passageway and secured to the housing side wall generally at the open end of the filter element such that the closed end of the filter element is downstream of the open end; and a cross-support extending generally laterally within the passageway at the closed end of the filter element for supporting the filter element within the passageway.

11. A filter chamber component as set forth in claim 10 further comprising at least two arms secured at proximal ends thereof to the side wall of the housing within the passageway and extending generally longitudinally within the passageway adjacent the side wall of the filter element to distal ends of said arms, the cross-support being connected to the distal ends of the arms and extending therebetween generally at the closed end of the filter element for supporting the filter element within the passageway.

12. A filter chamber component for filtering fluid flowing through an administration set, said filter chamber component comprising:

a generally tubular housing having an inlet for receiving fluid into the housing, an outlet for exhausting fluid from the housing, and aside wall defining a passageway through which fluid flows from the inlet toward the outlet of the housing, said side wall having a thickened portion extending radially inward therefrom; and a filter element constructed of a woven material and having a sack configuration including an open end, a closed end and a side wall therebetween, said filter element being disposed within the passageway and being molded into the side wall generally at the open end of the filter element whereby material from which the side wall is constructed passes through the woven material of the filter element at the open end thereof to secure the filter element within the housing side wall.

* * * * *